United States Patent [19]

Rooney et al.

[11] 4,423,063

[45] Dec. 27, 1983

[54] 2,4-DIOXO-4-SUBSTITUTED-1-BUTAOIC ACID DERIVATIVES USEFUL IN TREATING URINARY TRACK CALCIUM OXALATE LITHIASIS

[75] Inventors: Clarence S. Rooney, Worcester, Pa.; Haydn W. R. Williams, Dollard des Ormeaux, Canada; Edward J. Gragoe, Jr., Lansdale, Pa.; Arthur A. Patchett, Westfield, N.J.

[73] Assignee: Merck & Co., Inc., Rahway, N.J.

[21] Appl. No.: 354,995

[22] Filed: Mar. 5, 1982

Related U.S. Application Data

[62] Division of Ser. No. 220,648, Dec. 29, 1980, Pat. No. 4,337,258.

[51] Int. Cl.³ .............. A61K 31/335; A61K 31/235; A61K 31/19; C07C 149/40
[52] U.S. Cl. .................... 424/278; 549/350; 560/17; 560/18; 424/308; 424/317; 562/432; 546/301
[58] Field of Search .................... 549/350; 560/17, 18; 424/278, 308, 317; 562/432

[56] References Cited

U.S. PATENT DOCUMENTS 3,306,913  2/1967  Augstein et al. .................... 549/350

Primary Examiner—Henry R. Jiles
Assistant Examiner—Robert C. Whittenbaugh
Attorney, Agent, or Firm—Raymond M. Speer; Alice O. Robertson; Thomas E. Arther

[57] ABSTRACT

2,4-Dioxo-4-substituted-1-butanoic acid derivatives of the formula:

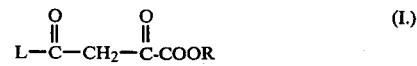

(I.)

where
R is hydrogen or $C_{1-4}$ alkyl; and
L is a lipophilic group consisting essentially of

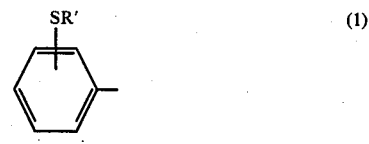

(1)

where R' is (a) hydrogen; (b) $C_{1-3}$ alkyl; (c) benzyl; (d) pyridyl $C_{1-3}$ alkyl or (e) (3,4-dihydro-3-hydroxy-2H-1,5-benzodioxepin-3-yl) methyl; provided that positions 2 and 6 of the substituted phenyl moiety may not be substituted; or

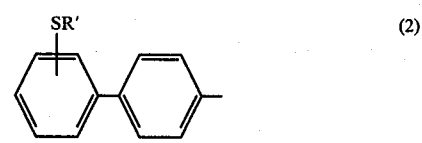

(2)

where R' has the same meaning as above;
or a pharmaceutically acceptable salt thereof; useful in treating urinary tract, especially renal calcium oxalate lithiasis.

7 Claims, No Drawings

2,4-DIOXO-4-SUBSTITUTED-1-BUTAOIC ACID DERIVATIVES USEFUL IN TREATING URINARY TRACK CALCIUM OXALATE LITHIASIS

This is a division of application Ser. No. 220,648, filed Dec. 29, 1980, now U.S. Pat. No. 4,337,258.

BACKGROUND OF THE INVENTION

1. Field of the Invention

The present invention is concerned with novel 2,4-dioxo-4-substituted-1-butanoic acid compounds useful in treating urinary tract, especially renal calcium oxalate lithiasis. The novel compounds of the present invention act as potent inhibitors of the enzyme glycolate oxidase.

The present invention is also concerned with a method of treating or preventing the formation of calcium oxalate urinary tract lithiasis, especially kidney or bladder stones, as well as pharmaceutical compositions useful in such a method, containing the novel 2,4-dioxo-4-substituted-1-butanoic acid compounds as active ingredient.

Close to 70% of kidney stones are composed partially or predominantly of calcium oxalate; yet there is no satisfactory drug specific for the treatment of calcium oxalate urinary tract lithiasis, nor for prophylactic use by people prone to recurrent attacks of this disease.

Calcium oxalate lithiasis, the formation of stony concretions composed partially or predominantly of calcium oxalate, may occur at different points in the urinary tract, and is especially a problem in the kidney and in the bladder.

Approximately 70% of all renal calculi contain oxalate as the main anionic component of the matrix. In many, but not all patients, the condition is associated with a higher than normal level of metabolically produced oxalate.

Common procedures for treatment of renal lithiasis due to calcium oxalate consist of surgical removal of stones, or control of the diet to restrict intake of calcium and/or oxalate combined with ingestion of large quantities of water to dilute the urine. Attempts at chemotherapy have included the administration of magnesium oxide, orthophosphate, cellulose phosphate, isocarboxazide, thiazide diuretics, allopurinol and succinimide. Limited success has been realized so far by these drug approaches. No drug which specifically inhibits the biosynthetic formation of oxalic acid is available for the treatment of calcium oxalate urinary tract, especially renal lithiasis.

The major precursor of oxalate is glyoxylate. Thus, approaches to the reduction of the biosynthetic output of oxalic acid focus on (a) the prevention of the conversion of glyoxylate to oxalate, and/or (b) restriction of the production of glyoxylate from its precursors. A major pathway for the biosynthesis of oxalate can be represented as follows:

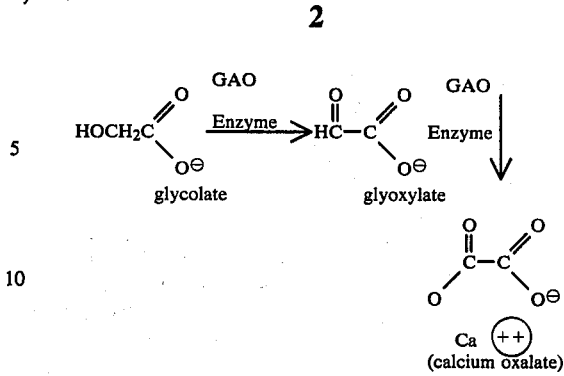

The same enzyme glycolate oxidase participates both in the biosynthesis of glyoxylate and, in its oxidation to oxalate. An inhibitor of the enzyme will act to block at two key points in the chain of reactions contributing to the production of oxalic acid. As a direct consequence of reducing oxalic acid levels in the urine with the compounds of this invention, the formation of oxalate calculi will be reduced or prevented in individuals whose urinary oxalate is primarily of metabolic origin.

The novel 2,4-dioxo-4-substituted-1-butanoic acid compounds described herein are potent inhibitors of glycolate oxidase and are thus useful in the treatment and prevention of urinary tract lithiasis, especially renal disease due to calcium oxalate stone formation in the kidney. As inhibitors of glycolate oxidase, the novel compounds of the present invention may also be useful in the treatment of primary hyperoxaluria. In the genetically inherited diseases designated hyperoxaluria types I and II, large quantities of oxalic acid are produced metabolically. Crystallization of calcium oxalate, occurring not only in the kidney and bladder, but in other tissues as well, frequently results in early death. The novel compounds of this invention may prove of value in the treatment of these rare but serious disease states.

2. Brief Description of the Prior Art

Glycolic acid oxidase inhibitors are described in U.S. Pat. Nos. 4,178,386; 4,207,329; and 4,233,452. Diketo fatty acids are described in Breusch and Keskin, *Enzymologia* 11, 356–60 (1945). 4-Aryl-3-bromo-2,4-dioxobutyrate esters are described in Andreichikov et al., U.S.S.R. Pat. No. 466-208. Ethyl p-phenylbenzoylpyruvate is described in Fatutta and Balestra, *Gazz. chim. ital.*, 88, 899–909 (1958). However, none of the compounds described in any of the above would suggest the novel 2,4-dioxo-4-substituted-1-butanoic acid compounds of the present invention.

SUMMARY OF THE INVENTION

The novel 2,4-dioxo-4-substituted-1-butanoic acid compounds of the present invention which are useful in treating and preventing urinary tract calcium oxalate lithiasis, especially the formation of calcium oxalate kidney or bladder stones, can be shown by the following formula:

where
R is hydrogen or $C_{1-4}$ alkyl; and
L is a lipophilic group consisting essentially of

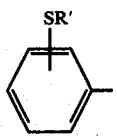
(1)

where R' is (a) hydrogen; (b) $C_{1-3}$ alkyl; (c) benzyl; (d) pyridyl $C_{1-3}$ alkyl; or (e) (3,4-dihydro-3-hydroxy-2H-1,5-benzodioxepin-3-yl) methyl; provided that postions 2 and 6 of the substituted phenyl moiety may not be substituted; or

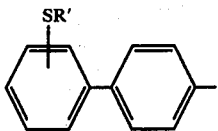
(2)

where R' has the same meaning as above; or a pharmaceutically acceptable salt thereof.

The enolic tautomer forms of the novel compounds of Formula I are also understood to be included within the scope of the present invention. These enol forms may be shown by the following formulas:

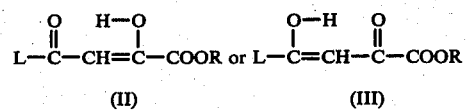

Particularly preferred compounds of Formula I are the following:

4-[(4'-methylthio-1,1'-biphenyl)-4-yl]-2,4-dioxo-1-butanoic acid

4-[[4'-[(3,4-dihydro-3-hydroxy-2H-1,5-benzodioxepin-3-yl)methylthio]-1,1'-biphenyl]-4-yl]-2,4-dioxo-1-butanoic acid 4-[[4'-[(p-phenylmethyl)thio]-1,1'-biphenyl]-4-yl]-2,4-dioxo-1-butanoic acid 4-[(4'-mercapto-1,1'-biphenyl)-4-yl]-2,4-dioxo-1-butanoic acid 4-[[4'-[2-(4-pyridinylethyl)thio]-1,1'-biphenyl]-4-yl]-2,4-dioxo-1-butanoic acid Included within the scope of the present invention are the pharmaceutically acceptable salts of the 2,4-dioxo-4-substituted-1-butanoic acid compounds.

Formula I compounds are organic acids with a pka in the range of 2 to 5 and thus can be used in the form of salts derived from inorganic or organic bases. Included among such salts are the following: metallic cations such as aluminum, calcium, lithium, magnesium, potassium, sodium and zinc; and organic cations such as choline, diethanolammonium, n-methylglucammonium, ethanolammonium, diethylammonium, and triethanolammonium. Neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt. Water or oil-soluble or dispersible products are thereby obtained.

Formula I compounds can be administered to patients (both human and animal) having, or being prone, to calcium oxalate kidney or bladder stone disease by formulating them in a composition such as tablet, capsule or elixir for oral administration. Sterile solutions or suspensions can be used for parenteral administration. About 25 to 500 mg of a compound of Formula I or a pharmaceutically acceptable salt is compounded with a pharmaceutically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose administered to patients having or prone to calcium oxalate kidney or bladder stone disease will be in the 50 mg to 2000 mg range with a preferred daily dose being 100 mg to 1000 mg of active ingredient. It will be realized by those skilled in the art that the dosage range for any particular patient (animal or human) will depend upon the severity of the disease treated, weight of the patient and any other condition which the physician or other person skilled in the art will take account of.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such a magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye, and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The 2,4-dioxo-4-substituted-1-butanoic acid compounds of Formula I may be prepared in accordance with a reaction scheme which may be illustrated as follows:

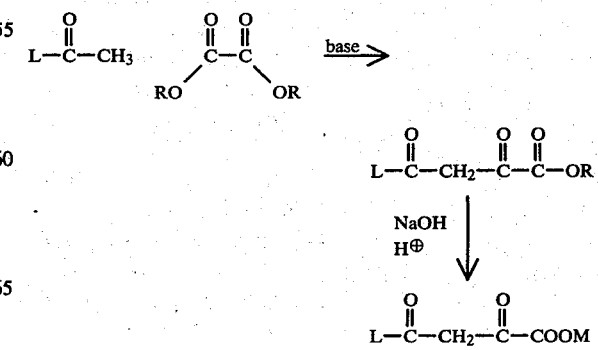

where R'' is $C_{1-4}$ alkyl, preferably methyl or ethyl; and L has the same meaning as above.

The methyl ketone starting materials are prepared by acetylation of a compound L-H with acetyl chloride or acetic anhydride and a Lewis acid catalyst under conventional Friedel-Crafts conditions, or by other routes well known in the art.

The first step of the reaction, in which the substituted methyl ketone is reacted with $C_{1-4}$ alkyl oxalate, can be carried out in solvents such as benzene, tetrahydrofuran, dimethylformamide, dioxane, and the like, in the presence of strong bases such as sodium or potassium methoxides, ethoxides, or butoxides, at temperatures from 0° to 50° C.

Following are examples which illustrate the preparation of representative compounds and compositions falling within the present invention, although no limitation is thereby intended.

EXAMPLE 1

4-[(4'-Mercapto-1,1'-biphenyl)-4-yl]-2,4-dioxo-1-butanoic acid

Step A
O-[(4'-Acetyl-1,1'-biphenyl)-4-yl]dimethylthiono carbamate

To a solution of 4-acetyl-4'-hydroxy-1,1'-biphenyl (15.9 g, 0.075 Mol) in dimethylformamide (110 ml) cooled in an ice bath is added sodium hydride (1.98 g, 0.0825 Mol) in four portions. in order to complete the reaction, the mixture may be warmed to 70° C., until unreacted sodium hydride is no longer evident. To the mixture, at ice bath temperature, is added dimethyl thiocarbamoyl chloride (11.6 g, 0.094 Mol) dropwise over 15 minutes. The reaction mixture is stirred at ice bath temperature for 15 minutes, then at room temperature overnight. The reaction is worked up by pouring over ice, and extracting the product into methylene chloride. The methylene chloride extract is washed with dilute sodium hydroxide, and water, and dried ($MgSO_4$). On evaporation, followed by recrystallization from acetonitrile there is obtained 13.8 g of the title compound, m.p. 154°–156° C.

Anal. Calc'd for $C_{17}H_{17}NO_2S$: % C, 68.20; % H, 5.72; % N, 4.68; % S, 10.71. Found: % C, 68.14; % H, 5.93; % N, 4.81; % S, 11.03.

Step B:
S-[(4'-Acetyl-1,1'-biphenyl)-4-yl]dimethylthiocarbamate

O-[4'-Acetyl-(1,1'-biphenyl)-4-yl]dimethylthiocarbamate (12.37 g, 0.041 Mol) is heated under a nitrogen atmosphere at 255°–260° C. for 2 hours and then allowed to cool. Recrystallization from acetonitrile gives 11.2 g, m.p. 178°–180° C., of the title compound.

Anal. Calc'd for $C_{17}H_{17}NO_2S$: % C, 68.20; % H, 5.72; % N, 4.68; % S, 10.71. Found: % C, 67.82; % H, 5.65; % N, 4.80; % S, 10.89.

Step C: 4'-Acetyl-4-mercapto-1,1'-biphenyl

A suspension of S-[4'-acetyl-(1,1'-biphenyl)-4-yl]dimethylthiocarbamate (0.90 g, 0.003 Mol) in methanol (45 ml) and 2 N sodium hydroxide (3.75 ml) is heated at reflux under a nitrogen atmosphere for 6 hours. The solution is acidified with 10% hydrochloric acid (3 ml), and the resulting suspension diluted with ice water (50 ml), and then extracted with methylene chloride. The dried ($MgSO_4$) extract is evaporated to give a cream-colored powder. The solid is dissolved in hot toluene (5 ml). After filtration, there is added isopropyl ether (10 ml), and petroleum ether (10 ml). The product is allowed to crystallize overnight. There is obtained a first crop product, along with a second crop after concentration of the filtrate, amounting to 0.32 g, m.p. 126°–128° C.

Anal. Calc'd for $C_{14}H_{12}OS$:
% C, 73.65; % H, 5.30; % S, 14.04. Found: % C, 73.76; % H, 5.50; % S, 13.85.

Step D: Ethyl [(4'-Mercapto-1,1'-biphenyl)-4-yl]-2,4-dioxo-1-butanoate

To a suspension of sodium hydride (0.81 g, 0.034 Mol) in dimethylformamide (6 ml) is added ethanol (1.93 g, 0.042 Mol) dropwise with stirring and ice cooling. When hydrogen evolution has ceased, a solution of 4'-acetyl-4-mercapto-1,1'-biphenyl (2.74 g, 0.012 Mol) and diethyl oxalate (3.07 g, 0.021 Mol) in dimethylformamide (18 ml) is added slowly over 1 hour. The reaction mixture is stirred for 3 hours at room temperature and then poured slowly into ice water (300 ml) containing 2 N hydrochloric acid (21 ml). The yellow solid crude product is filtered, and then dried thoroughly in vacuum. The solid is dissolved in hot benzene (15 ml) and the solution filtered through Celite. Petroleum ether (10 ml) is added to the filtrate to induce crystallization. There is obtained 3.3 g of the title compound, m.p. 90°–95° C.

Anal. Calc'd. for $C_{18}H_{16}O_4S$: % C, 65.84; % H, 4.91; % S, 9.76. Found: % C, 66.12; % H, 4.89; % S, 9.52.

Step E:
4-[(4'-Mercapto-1,1'-biphenyl)-4-yl]-2,4-dioxo-1-butanoic acid

To a solution of ethyl 4-[4'-mercapto-(1,1'-biphenyl)-4-yl]-2,4-dioxo-1-butanoate (1.97 g, 0.006 Mol) in tetrahydrofuran (50 ml) is added 7.5 ml of 2.5 N sodium hydroxide. The reaction mixture is allowed to stir under nitrogen for 8 hours. The reaction mixture is acidified to pH about 1.5 with 2 N hydrochloric acid (-8 ml), and then nitrogen is passed through the mixtures for 1 hour to reduce the content of tetrahydrofuran. Water (10 ml) is added, and after stirring 20 minutes, the solids are collected by filtration. The dry solid is dissolved in hot tetrahydrofuran-ethyl acetate (1:1) (13 ml) and the hot solution treated with charcoal and filtered. The filtrate is evaporated and the residue slurried in ethyl acetate (10 ml) and filtered to give 1.5 g of nearly pure 4-[4'-mercapto-(1,1'-biphenyl)-4-yl]-2,4-dioxo-1-butanoic acid. The solid is dissolved in hot tetrahydrofuran-ethyl acetate (1:2) (7.5 ml) and the solution filtered. The filtrate is evaporated and the solid residue slurried with ethyl acetate (5 ml) and filtered to give 0.57 g of product, m.p. 185.5°–187° C. (dec).

Anal. Calc'd for $C_{16}H_{12}O_4S$: % C, 63.99; % H, 4.03; % S, 10.68. Found: % C, 63.44; % H, 4.40; % S, 10.38.

EXAMPLE 2

[(4'-Methylthio-1,1'-biphenyl)-4-yl]-2,4-dioxo-1-butanoic acid

Step A: 1-Acetyl-4'-methylthio-1,1'-biphenyl

To a mixture of refluxing methanol (135 ml) containing 2 N sodium hydroxide (11.25 ml), which has been flushed with nitrogen to remove dissolved oxygen, is added S-[(4'-acetyl-1,1'-biphenyl)-4-yl]dimethylthiocarbamate (Example 1, Step B) (2.7 g, 0.009 Mol). The mixture is refluxed overnight under nitrogen, and then there is added simultaneously 10 N sodium hydroxide (10.9 ml) and dimethyl sulfate (0.86 ml, 0.009 Mol). Refluxing is continued for 2 hours. Additional 10 N sodium hydroxide (0.8 ml) is added. After refluxing one additional hour, the reaction mixture is cooled and then poured over ice. A light brown solid is obtained which is filtered, washed well with water and dried, m.p. 182°–183.5° C.

Anal. Calc'd for $C_{15}H_{14}OS$: % C, 74.34; % H, 5.82; %S, 13.23. Found: % C, 74.30; % H, 5.75; %S, 13.56.

Step B: Methyl 4-[(4'-methylthio-1,1'-biphenyl)-4-yl]-2,4-dioxo-1-butanoate

To a mixture of anhydrous sodium methoxide (1.15 g, 0.02 Mol) in dimethylformamide (100 ml) under a nitrogen atmosphere is added a mixture of dimethyl oxalate (1.42 g, 0.012 Mol) and 1-acetyl-4'-methylthio-1,1'-biphenyl (1.3 g, 0.0054 Mol) in dimethylformamide (50 ml). The mixture is allowed to react at room temperature for 4 hours and then at 50° C. for 2 hours. It is then cooled to room temperature and poured onto ice. After acidification with 5 N hydrochloric acid, the product is extracted with ethyl acetate. Evaporation of the ethyl acetate extract, followed by two recrystallizations of the residue from acetonitrile provides the title compound as a yellow solid, m.p. 141°–143° C.

Anal. Calc'd for $C_{18}H_{16}O_4S$: % C, 65.83; % H, 4.91; % S, 9.76. Found: % C, 65.63; % H, 4.75; % S, 9.80.

Step C: 4-[(4'-Methylthio-1,1'-biphenyl)-4-yl]-2,4-dioxo-1-butanoic acid

To methyl 4-[4'-methylthio-(1,1'-biphenyl)-4-yl]-2,4-dioxo-1-butanoate (0.33 g, 0.001 Mol) in ethanol (10 ml) is added dioxane (0.6 ml) and 2 N potassium hydroxide (1.5 ml, 0.003 Mol). The mixture is stirred at room temperature for 5 hours. After acidification with 6 N hydrochloric acid, the product is partitioned between ethyl acetate and water. After drying (MgSO4), the ethyl acetate extract is evaporated, and the residue is recrystallized from acetonitrile to give the title compound, m.p. 191°–195° C.

Anal. Calc'd for $C_{17}H_{14}O_4S$: % C, 64.95; % H, 4.49; % S, 10.19. Found: % C, 64.65; % H, 4.85; % S, 10.06.

EXAMPLE 3

4-[[4'-[(3,4-Dihydro-3-hydroxy-2H-1,5-benzodioxepin-3-yl)-methylthio]-1,1'-biphenyl]-4-yl]-2,4-dioxo-1-butanoic Acid

Step A: Ethyl 4-[[4'-[(3,4-dihydro-3-hydroxy-2H-1,5-benzodioxepin-3-yl)methylthio]-1,1-biphenyl]-4-yl]-2,4-dioxo-1-butanoate A mixture of ethyl 4-[4'-mercapto-(1,1'-biphenyl)-4-yl]-2,4-dioxo-1-butanoate (1.87 g, 0.006 Mol) and 3,4-dihydro-2H-1,5-benzodioxepin-3-spirooxirane (1.12 g, 0.0063 Mol) in dry tetrahydrofuran is filtered, and then placed in a flask with a nitrogen atmosphere. After addition of triethylamine (1.2 ml), the reaction is stirred overnight at room temperature. Following evaporation, the residue is recrystallized from acetonitrile (10 ml) giving product, m.p. 113°–117° C.

Step B: 4-[[4'-[(3,4-Dihydro-3-hydroxy-2H-1,5-benzodioxepin-3-yl)methylthio]-1,1'-biphenyl]-4-yl]-2,4-dioxo-1-butanoic acid A mixture of ethyl 4-[[4'-[(3,4-dihydro-3-hydroxy-2H-1,5-benzodioxepin-3-yl)methylthio]-1,1'-biphenyl]-4-yl]-2,4-dioxo-1-butanoate (0.51 g, 0.001 Mol), 1 N sodium hydroxide (2.5 ml), and tetrahydrofuran (5 ml) is stirred under nitrogen for 8 hours. Following acidification with 2 N hydrochloric acid (1.25 ml), a yellow solid gradually forms. Following filtration and drying, the product is added to hot tetrahydrofuran (24 ml), and the mixture filtered. Acetonitrile (24 ml) is added to the filtrate and crystals are allowed to form overnight in the refrigerator. The title product is obtained by filtration, m.p. 218°–219° C. (dec).

Anal. Calc'd for $C_{26}H_{22}O_7S$: % C, 65.26; % H, 4.63; % S, 6.70. Found: % C, 64.78; % H, 4.85; % S, 6.91.

EXAMPLE 4

4-[[4'-[(Phenylmethyl)thio]-1,1'-biphenyl]-4-yl]-2,4-dioxo-1-butanoic acid

Step A: Ethyl 4-[[4'-[(phenylmethyl)thio]-1,1'-biphenyl)-4-yl]-2,4-dioxo-1-butanoate To a mixture of ethyl 4-[(4'-mercapto-1,1'-biphenyl)-4-yl]-2,4-dioxo-1-butanoate (3.28 g, 0.01 Mol) in tetrahydrofuran (35 ml) is added N,N-diisopropylethylamine (2.7 g, 0.021 Mol). After cooling to ice temperature, a solution of benzyl bromide (1.88 g, 0.011 Mol) in tetrahydrofuran is added. After stirring at room temperature 5 hours, the reaction mixture is filtered, and the filtrate evaporated to about one-third volume. The solid is filtered, dried, and recrystallized from acetonitrile to give the title compound, m.p. 122°–124° C.

Anal. Calc'd for $C_{25}H_{22}O_4S$: % C, 71.74; % H, 5.29; %S, 7.66. Found: % C, 71.78; % H, 5.34; %S, 7.86.

Step B: 4-[[4'-[(Phenylmethyl)thio]-1,1'-biphenyl]-4-yl]-2,4-dioxo-1-butanoic acid To a mixture of ethyl 4-[[4'-[(phenylmethyl)thio]-1,1'-biphenyl]-4,yl]-2,4-dioxo-1-butanoate (1.2 g, 0.003 Mol) in tetrahydrofuran (15 ml) is added dropwise 1 N sodium hydroxide (7.5 ml). The mixture is allowed to stir at room temperature under nitrogen for 5 hours. Following acidification with 2 N hydrochloric acid, the solid which forms is filtered, and washed with a small amount of tetrahydrofuran, and then water. Recrystallization from acetonitrile gives the title compound, m.p. 208°–210° C.

Anal. Calc'd for $C_{23}H_{18}O_4S$: % C, 70.75; % H, 4.64. Found: % C, 70.46; % H, 4.93.

EXAMPLE 5

4-[[4'-[2-(4-Pyridinylethyl)thio]-1,1'-biphenyl]-4-yl]-2,4-dioxo-1-butanoic acid

Step A: Ethyl 4[[4'-[2-(4-Pyridinylethyl)thio]-1,1-biphenyl]-4-yl]-2,4-dioxo-1-butanoate To a mixture of ethyl 4[(4'-mercapto-1,1'-biphenyl)-4-yl]-2,4-dioxo-1-butanoate (0.33 g, 0.001 Mol) in tetrahydrofuran (5 ml) is added 4-vinylpyridine (0.105 g, 0.001 Mol). The mixture is allowed to stand overnight under a nitrogen atmosphere. Evaporation of the solvent leaves a yellow solid which is recrystallized from acetonitrile (10 ml) to give 0.21 g of the title compound, m.p. 108°–110° C.

Anal. Calc'd for $C_{25}H_{23}NO_4S$: % C, 69.26; % H, 5.34; % N, 3.23. Found: % C, 69.36; % H, 5.35; % N, 3.30.

Step B:
4-[[4'-[2-(4-Pyridinylethyl)thio]-1,1'-biphenyl]-4-yl]-2,4-dioxo-1-butanoic acid To a mixture of ethyl 4-[[4'-[2-(4-pyridinylethyl)thio]-1,1'-biphenyl]-4-yl]-2,4-dioxo-1-butanoate (0.22 g, 0.0005 Mol) and tetrahydrofuran (5 ml) is added 2 N sodium hydroxide (0.63 ml, 0.00125 Mol). The reaction is allowed to proceed under nitrogen for 4 hours. Acidification with 2 N hydrochloric acid (0.63 ml) followed by the addition of water (25 ml) results in the formation of solid product. After drying, the crude solid is recrystallized from dimethylformamide. The melting point of a pure sample is 221°–222.5° C.

Anal. Calc'd for $C_{23}H_{19}NO_4S$: % C, 68.13; % H, 4.72; % N, 3.45. Found: % C, 67.83; % H, 4.57; % N, 3.75.

EXAMPLE 6

Dry-filled Capsules Containing 50 mg. of Active Ingredient per Capsule

| Ingredient | Amount per Capsule |
|---|---|
| 4-[(4'-methylthio-1,1'-biphenyl)-4-yl]-2,4-dioxo-1-butanoic acid | 50 mg. |
| Lactose | 149 mg. |
| Magnesium Stearate | 1 mg. |
| Capsule (Size No. 1) | 200 mg. |

The active ingredient is reduced to a No. 60 powder and then the lactose and magnesium stearate are passed through a No. 60 bolting cloth onto the powder, and the combined ingredients are admixed for 10 minutes and then filled into a No. 1 dry gelatin capsule.

EXAMPLE 7

Glycolate Oxidase Enzyme Inhibition

The usefulness of the compounds of the present invention in treating urinary tract, especially renal, calcium oxalate lithiasis, is shown by the ability of those compounds to inhibit the glycolate oxidase enzyme. This inhibition was determined by observing the extent to which the test compound blocked the activity of the enzyme. The activity of the enzyme, in turn, was measured by following the rate of reduction of sodium 2,6-dichlorophenol-indophenol by sodium glycolate in the presence of the enzyme. The enzyme was pig liver glycolate oxidase. The reaction was followed spectrophotometrically at 600 nm. The assay was conducted at 25° C. in a 0.10 M phosphate buffer, pH 7.0, containing 3 mM EDTA. Initial substrate concentrations were $5 \times 10^{-5}$ M of sodium 2,6-dichlorophenol-indophenol and $2 \times 10^{-4}$ M of sodium glycolate. Reactions were initiated by the addition of enzyme. Initial rates during the period from 1 to 3 min. after the addition of enzyme were recorded on a Beckman Acta M-VI spectrophotometer. One control was run simultaneously with three test reactions and all initial rates were adjusted to a common control rate. For further details of this procedure, see Randall et al., *J. Med. Chem.*, 22, 6, 612 (1979).

The results obtained from this assay are illustrated below.

| Compound | $IC_{50}$ |
|---|---|
| 4-[(4'-methylthio-1,1'-biphenyl)-4-yl]-2,4-dioxo-1-butanoic acid | $1.5 \times 10^{-7}$ |
| 4-[[4'-[(3,4-dihydro-3-hydroxy-2H—1,5-benzodioxepin-3-yl)methylthio]-1,1']-biphenyl]-4-yl]-2,4-dioxo-1-butanoic acid | $6.2 \times 10^{-8}$ M |
| 4-[[4'-[(phenylmethyl)thio]-1,1'-biphenyl]-4-yl]-2,4-dioxo-1-butanoic acid | $4.2 \times 10^{-7}$ M |
|  | $2.1 \times 10^{-6}$ M |

-continued

| Compound | $IC_{50}$ |
|---|---|
| 4-[(4'-mercapto-1,1'-biphenyl)-4-yl]-2,4-dioxo-1-butanoic acid | |
| 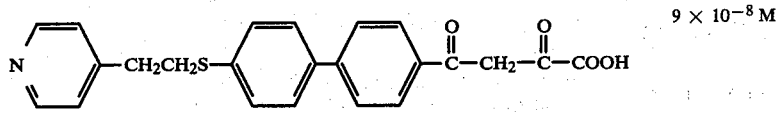 | $9 \times 10^{-8}$ M |
| 4-[[4'-[2-(4-pyridinylethyl)thio]-1,1'-biphenyl]-4-yl]-2,4-dioxo-1-butanoic acid | |

What is claimed is:

1. A compound of the formula:

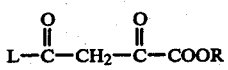

where
R is hydrogen or $C_{1-4}$ alkyl; and
L is a lipophilic group having the structure:

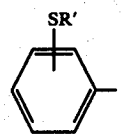

where R' is (a) hydrogen; (b) $C_{1-3}$ alkyl; (c) benzyl; or (d) (3,4-dihydro-3-hydroxy-2H-1,5-benzodioxepin-3-yl)methyl; provided that positions 2 and 6 of

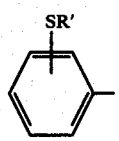

may not be substituted; or

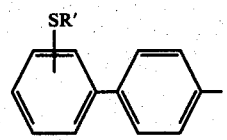

where R' has the same meaning as above; or a pharmaceutically acceptable salt thereof.

2. A compound according to claim 1 wherein the compound is
4-[(4'-methylthio-1,1'-biphenyl)-4-yl]-2,4-dioxo-1-butanoic acid.

3. A compound according to claim 1 wherein the compound is
4-[[4'-[(3,4-dihydro-3-hydroxy-2H-1,5-benzodioxepin-3-yl)methylthio]-1,1'-biphenyl]-4-yl]-2,4-dioxo-1-butanoic acid.

4. A compound according to claim 1 wherein the compound is
4-[[4'-[(phenylmethyl)thio]-1,1'-biphenyl-4-yl]-2,4-dioxo-1-butanoic acid.

5. A compound according to claim 1 wherein the compound is
4-[(4'-mercapto-1,1'-biphenyl)-4-yl]-2,4-dioxo-1-butanoic acid.

6. A method of treating or preventing the formation of calcium oxalate urinary tract lithiasis, especially kidney or bladder stones, which comprises administering to a patient with, or prone to, such disease a therapeutically effective amount of a compound of the formula:

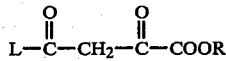

where
R is hydrogen or $C_{1-4}$ alkyl; and
L is a lipophilic group having the structure

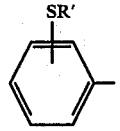

where R' is (a) hydrogen: (b) $C_{1-3}$ alkyl; (c) benzyl; or (d) (3,4-dihydro-3-hydroxy-2H-1,5-benzodioxepin-3-yl)methyl; provided that positions 2 and 6

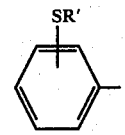

may not be substituted; or

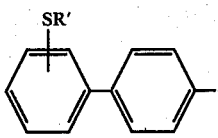

where R' has the same meaning as above;
or a pharmaceutically acceptable salt thereof.

7. A pharmaceutical composition for use in treating or preventing the formation of calcium oxalate urinary tract lithiasis, especially kidney or bladder stones, comprising a pharmaceutically acceptable carrier and a therapeutically effective amount of a compound of the formula:

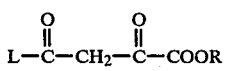
where
R is hydrogen or $C_{1-4}$ alkyl; and
L is a lipophilic group having the structure
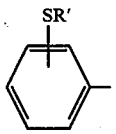 (1)
where R' is (a) hydrogen; (b) $C_{1-3}$ alkyl; (c) benzyl; or (d) (3,4-dihydro-3-hydroxy-2H-1,5-benzodioxe- pin-3-yl)methyl; provided that positions 2 and 6 of
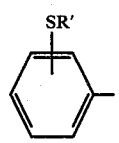
may not be substituted; or
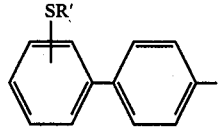 (2)
where R' has the same meaning as above; or a pharmaceutically acceptable salt thereof.
* * * * *